United States Patent [19]

Harris et al.

[11] Patent Number: 4,465,471

[45] Date of Patent: Aug. 14, 1984

[54] INTRAVENOUS ADMINISTRATION SYSTEM FOR DRY MEDICINE

[75] Inventors: Dale C. Harris, Fairland; William W. Hargrove, Indianapolis, both of Ind.

[73] Assignee: Eli Lilly and Company, Indianapolis, Ind.

[21] Appl. No.: 401,874

[22] Filed: Jul. 26, 1982

Related U.S. Application Data

[63] Continuation-in-part of Ser. No. 296,335, Apr. 26, 1981, abandoned.

[51] Int. Cl.$^3$ .............................................. A61M 5/14
[52] U.S. Cl. ........................................ 604/56; 604/85; 604/92; 604/406
[58] Field of Search ........................... 604/56, 82–88, 604/244, 251, 252, 255, 262, 403, 405, 406, 408, 411, 413–416, 92; 141/329, 330; 422/264

[56] References Cited

U.S. PATENT DOCUMENTS

| | | | |
|---|---|---|---|
| 927,826 | 7/1909 | Breitmeyer . | |
| 1,086,976 | 2/1914 | Abramovitz . | |
| 1,718,593 | 6/1929 | Smith . | |
| 1,889,111 | 11/1932 | Serr . | |
| 1,931,765 | 10/1933 | Leever . | |
| 1,945,351 | 1/1934 | Grafton . | |
| 2,058,901 | 10/1936 | McPherson . | |
| 2,067,328 | 1/1937 | Lux . | |
| 2,292,673 | 8/1942 | Taylor et al. . | |
| 2,332,030 | 10/1943 | Toronto . | |
| 2,371,720 | 3/1945 | Stine . | |
| 2,462,886 | 3/1949 | Morrow | 422/264 |
| 2,573,576 | 10/1951 | Klumb . | |
| 2,584,910 | 2/1952 | Ohlwiler . | |
| 2,653,611 | 9/1953 | Smith . | |
| 2,663,298 | 12/1953 | Rose . | |
| 2,696,963 | 12/1954 | Shepherd . | |
| 2,731,965 | 1/1956 | Haralson, Jr. . | |
| 2,854,977 | 10/1958 | McConnaughey . | |
| 2,885,271 | 5/1959 | Kersh . | |
| 2,900,100 | 8/1959 | Debat et al. . | |
| 2,923,293 | 2/1960 | Nawoj et al. . | |
| 2,971,850 | 2/1961 | Barton . | |
| 3,000,540 | 9/1961 | Wheeler . | |
| 3,001,525 | 9/1961 | Hendricks | 128/214 C |
| 3,003,500 | 10/1961 | Barton et al. . | |
| 3,128,917 | 4/1964 | Krause . | |
| 3,135,259 | 6/1964 | Evans . | |
| 3,165,114 | 1/1965 | Garrett . | |
| 3,191,915 | 6/1965 | Goettl . | |
| 3,273,704 | 9/1966 | Rudiger . | |
| 3,305,446 | 2/1967 | Bechtol et al. . | |
| 3,340,888 | 9/1967 | Farison . | |
| 3,433,215 | 3/1969 | Silverman . | |
| 3,438,373 | 4/1969 | Pannier, Jr. . | |
| 3,788,524 | 1/1974 | Davis et al. | 128/214 C |
| 3,857,392 | 12/1974 | Ogle | 128/214 C |
| 4,161,178 | 7/1979 | Genese | 604/413 |
| 4,203,443 | 5/1980 | Genese | 604/413 |
| 4,217,894 | 8/1980 | Franetzki | 128/213 R |
| 4,265,760 | 5/1981 | Abel et al. | 604/262 |
| 4,298,358 | 11/1981 | Ruschke | 128/214 |
| 4,333,493 | 6/1982 | Beizwenger et al. | 422/264 |
| 4,335,717 | 6/1982 | Bujan et al. | 128/214 R |
| 4,340,054 | 7/1982 | Michaels | 128/260 |
| 4,392,850 | 7/1983 | Elias et al. | 604/416 |
| 4,392,851 | 7/1983 | Elias et al. | 604/413 |
| 4,410,321 | 10/1983 | Pearson et al. | 604/82 |
| 4,424,056 | 1/1984 | Urquhart et al. | 604/56 |

FOREIGN PATENT DOCUMENTS

| | | |
|---|---|---|
| 7820919 | 7/1978 | France . |
| WO81/01241 | 5/1980 | PCT Int'l Appl. . |
| 1461161 | 1/1977 | United Kingdom . |
| 2059776 | 4/1981 | United Kingdom . |

*Primary Examiner*—C. Fred Rosenbaum
*Assistant Examiner*—Michelle N. Lester
*Attorney, Agent, or Firm*—Barnes & Thornburg

[57] ABSTRACT

The system of this invention provides a method and apparatus for the sterile intravenous administration of dry medicine. Such a system can include standard IV set components such as a source of liquid, means to inject liquid into a human vein, means forming a passageway between the source of liquid and said injection means, a valve to control the flow of liquid through the passageway, and a cartridge-like dry medicine package adapted for use with the system. Such a package can include conduit means adapted to perforate and communicate with the passageway, means forming a cell for dry, particulate medicine with portions forming a liquid-pervious barrier to the dry medicine and an air vent with an air-pervious, liquid barrier. The perforating conduit means is in communication with the liquid-pervious barrier portion of the cell so that, upon perforation of the passageway means by the perforating conduit means below the source of liquid, the cell fills with liquid, the medicine is placed in solution in the liquid, and the medicine solution flows into the vein. Dry medicine can, for example, be administered intravenously in liquid solution in a variety of dosages and at a variety of rates without resort to a pharmacy by enclosing it in such a sterile package adapted for addition to an IV system at a patient's bedside.

9 Claims, 6 Drawing Figures

INTRAVENOUS ADMINISTRATION SYSTEM FOR DRY MEDICINE

This is a continuation-in-part of our prior co-pending application Ser. No. 06/296,335, filed Apr. 26, 1981, and now abandoned.

This invention relates to a system to administer a dry medicine intravenously.

Medical treatment frequently requires the administration of fluids and medication solutions intravenously. Such fluids can include saline and dextrose solutions and other solutions to correct imbalances in body chemistry and medication solutions to treat disease. Such solutions are frequently available in commercial aseptic solution containers that are adapted to be punctured at one end and be hung from the other end so that their liquid contents may be removed and infused in the vein of a patient.

In effecting such treatment, an intravenous administration set, commonly referred to as an IV set, is used to puncture the closure of the solution container and to conduct the liquid material from the solution container to a hypodermic needle for injection into the veins of the patient. Included in such IV sets are a transparent drip chamber having a conduit-forming spike at one end to perforate and enter the solution container, a transparent, flexible, plastic tube attached at the other end of the drip chamber, a regulating clamp providing means to control the flow of liquid through the passageway of the plastic tube, one or more Y injection sites to provide means to attach other medicament dispensers, and a termination adapted to accept a hypodermic needle. Such IV sets may include a vacuum pump adapted for insertion and operation in pump-operating apparatus. The use of the IV sets requires aseptic techniques, and the IV set is protected against contamination from handling at the point of attachments to the solution container and the hypodermic needle by protective end caps. In the administration of solutions and medication intravenously, liquid flow may be regulated through adjustment of the regulating clamp (or any volume pump that may be in use). Frequently, liquid medications are added piggyback to other liquid solutions by attaching the source of liquid medication at a Y injection site, preferably upstream of any pump that may be in use.

Certain medicines are manufactured and packaged in dry form because their stability is impaired in liquid solution. Antibiotics are frequently manufactured and packaged for storage and shipment in dry form because of their instability in liquid solution.

Where dry medicines have been administered intravenously in the past, liquid solutions of the dry medicines had to be prepared shortly before their administration commenced. In hospital treatment, this meant that the liquid solutions were prepared from dry medicines at the hospital pharmacy for delivery to those personnel responsible for their administration. Liquid solutions of many dry medicines are carefully prepared to avoid an injection of small particles of medicine into the veins of a patient because such particles of the medicine will "burn" or irritate the patient's veins, causing discomfort.

This invention provides a system for the administration of dry medicines by placing the dry medicine in solution at the patient's bedside with an IV set rather than in the pharmacy. In this invention, the container in which the dry medicine is packaged becomes a part of the intravenous administration system and is adapted to be added to a primary IV set, preferably adjacent the drip chamber. The package provides a sterile cartridge-like container for the dry medicine adapted for addition to such a system and for the sterile administration of its medicine.

The package includes perforating conduit means adapted to perforate a rubber stopper at any injection site in an IV administration set. The container walls of the package form a cell or compartment for the dry medicine. One portion of the cell or compartment is formed by a liquid-pervious barrier to the dry medicine, and the cell or compartment is provided with an air-pervious, liquid barrier. The portion of the cell formed by the liquid-pervious barrier is connected in communication with the perforating conduit means.

In a system adapted to administer dry medicine from such a package, an adapter, or a Y injection site, may be provided immediately adjacent and either above or below the drip chamber and below the level of liquid in the solution container. Treatment with the dry medicine can then be commenced by adding the package of dry medicine to the IV system at the injection site immediately adjacent the drip chamber. The package of dry medicine is added to the system by simply pressing the perforating conduit means through the rubber stopper at the injection site. Because the dry medicine container is below the level of liquid in the solution container, liquid flows through the IV set into the container through the perforating conduit means; air within the container is expelled through the air-pervious liquid barrier of the container; and liquid passes through the liquid-pervious barrier and fills the container. The resulting medicine solution passes outwardly through the liquid-pervious barrier and perforating conduit means of the container and into the IV set, which conveys it into the veins of the patient. Because the dry medicine container remains below the level of liquid in the solution container, the medicine solution leaving the dry medicine container is replaced by liquid from the solution container until such time as the medicine has been completely administered. The dry medicine package of the system may be provided with a single spike or needle, having a single or multiple passages, or multiple needles as desired.

The invention thus provides a method of administration of dry medicine intravenously by enclosing the dry medicine in a sterile package behind a liquid-pervious barrier to the dry medicine, adding the sterile package to an intravenous administration system for liquid solutions by placing the interior of the package in communication with the passageway of the intravenous administration set, admitting the liquid into the package and producing a medicine solution from the medicine and liquid, and permitting the solution of medicine to flow continuously from the package into the passageway for administration to a patient while providing a continuous replacement flow of liquid solution into the package.

The system can be designed to administer different dry medicines over different time periods and can permit repeated administrations on a scheduled interval. Since the dry medicine does not have to be prepared for intravenous administration at or by a hospital pharmacy, it can be stored and used by personnel on a hospital floor. Furthermore, the system is capable of implementation with many standard IV system components.

Further features and advantages of the invention will be apparent from the following drawings and descriptions.

Figure 1:
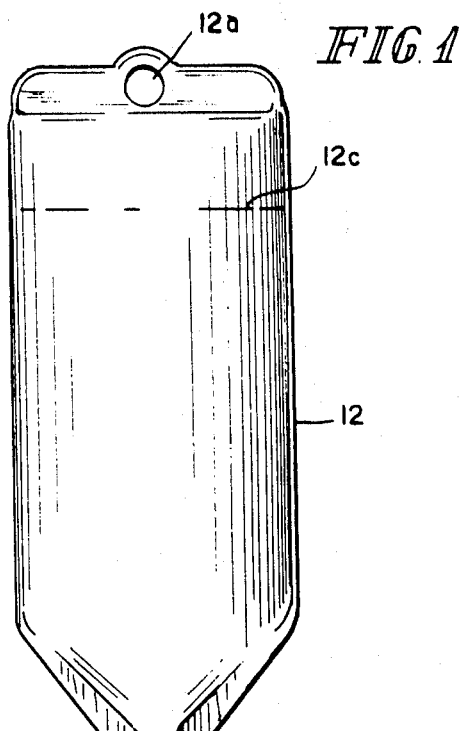
FIG. 1 is a drawing of a dry medicine, intravenous administration system of this invention.

The system 10 of this invention, shown in FIG. 1, includes a source of liquid 12 and an IV administration set 14 including a drip chamber 16 with an adjacent attachment connecting means 18, such as a standard Y injection site, and a regulating clamp 20, all interconnected by means 22a, 22b, forming a passageway between the drip chamber 16 and a hypodermic needle 24 which is shown inserted into the vein of a patient to deliver liquid from the system into the patient.

The source of liquid 12 may be a solution container, for example, of the type manufactured by Travenol Laboratories, Inc., of Deerfield, Ill. 60015, and sold under the registered trademark VIAFLEX as a single-dose container. Such containers are clear, flexible plastic provided with an opening 12a at one end so that the source of liquid 12 may be suspended above the patient and a conduit-like closure 12b at the other end adapted for perforation and sealing engagement with the IV set 14.

The IV set 14 includes components of the type typically distributed by Ivac Corporation of San Diego, Calif. 92121. In such a set, the drip chamber 16 is provided at one end with a spike-like conduit means 16a adapted to perforate and enter and provide a sealed engagement at its periphery with the conduit-like closure 12b of solution container 12. The central portion of the drip chamber 16b is formed from transparent plastic to permit visual monitoring of the rate at which liquid is flowing from the source of liquid 12 into the veins of the patient 26. The downstream end of the drip chamber 16c is attached to a transparent, flexible, plastic tube 22a to carry the liquid from the drip chamber 16. The Y injection site 18 provides means to attach and connect an additional source of medicine to the system. The Y injection site provides a sterile access to the passageway of the system which is closed by a standard rubber IV stopper 18a.

The flow of liquid from the source 12 is controllable through use of the regulating clamp 20. Such clamps can include a serrated roller adapted to engage the outer surface of flexible plastic tube 22b and to pinch, to a variable degree, and thereby impose a restriction upon the passageway of the tubing, controlling the rate at which liquid from source 12 passes the restriction formed in the tubing 22b by the regulating clamp 20.

The system of this invention includes a cartridge-like package or container 30 for dry medicine. The dry medicine may be in powdered form or may be a single body of medicine, which, for example, may comprise a compressed mass of particulate medicine. The cartridge-like package 30 may be added to the system 10 at the Y injection site, thereby permitting the dry medicine packaged in container 30 to be administered piggyback fashion with the liquid from source 12.

Figure 2:
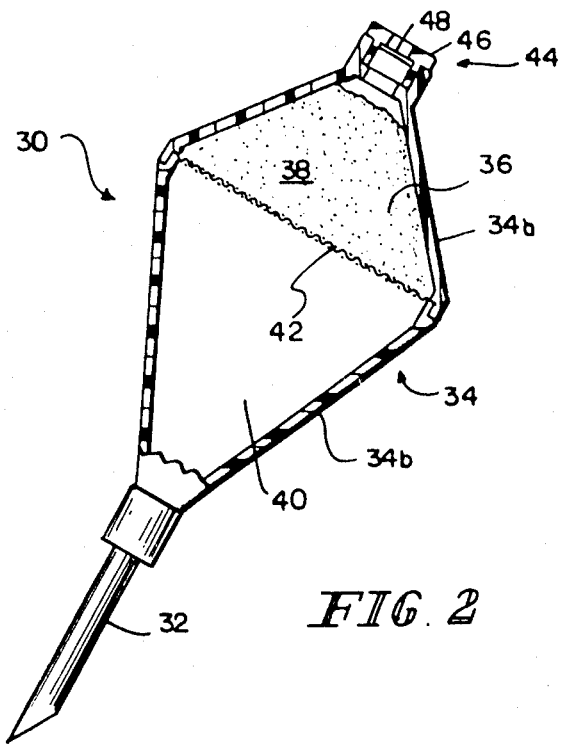
FIG. 2 is a cross-sectional view of the cartridge-like, dry-medicine package and container that is shown in FIG. 1.

FIG. 2 shows a partial cross-sectional view of the package 30, and its operation in the system may be determined by reference to FIG. 1 and FIG. 2. The package 30 includes a perforating conduit means 32, which may be a standard hypodermic needle or other sharpened tubular conduit specifically manufactured as part of the package 30. The package 30 includes means 34 forming at least a first cell or compartment 36 for dry medicine 38. The means 34 preferably forms a second cell 40, as will be explained. A liquid-pervious barrier 42 is interposed between the first cell 36 for dry, particulate medicine and the perforating conduit means 32 to prevent particles of medicine from entering the IV system 14. Where means 34 of the package forms two compartments, the barrier 42 may define a wall between the two compartments. The package 30 is provided with an air vent 44 at the end of the cartridge opposite perforating conduit means 32. The barrier 42 is pervious to air as well as liquid in package 30 to permit air in the second cell 40 to reach and escape through air vent 44. Air vent 44 is formed by an opening 46 in cell-forming means 34 that is closed by an air-pervious, liquid barrier 48. An example of such an air-pervious, liquid barrier is a fluoroplastic material sold by the FLURO TECHNIQUES Corporation under their designation M8A 2000. To avoid contamination of medicine within package 30, the air vent 44 may be recessed as shown or provided with an additional air-pervious outer shield to prevent contact with the air-pervious liquid barrier 48 as package 30 is handled. Cell-forming means 34 is preferably a molded transparent thermoplastic material so that the interior of the package 30 may be monitored visually in use.

The barrier 42 of the package may be any material which will transmit liquid but not particles of dry medicine having a size sufficient to reach and irritate the patient's veins. Such simple materials as common laboratory filter paper may function as a barrier in combination with a downstream filter to prevent paper fibers from being infused in the patient. Selection of the barrier material and its porosity is a major consideration in designing the system to provide different rates of drug administration. Another major consideration is the rate of solubility of the dry medicine in the liquid of the system. Where the dry medicine may pass rapidly into solution in the liquid of the system, selection of relatively non-porous barrier material will permit the rate of administration of the soluble medicine to be slowed and controlled. Where the dry medicine passes into solution very slowly (for examle, where a single body of dry medicine is relatively insoluble in the liquid), a porous barrier material may be selected having pore sizes only sufficiently small to prevent the passage of medicine particles that will burn or irritate a patient's veins. Thus, the package permits control of the rate of administration of many very soluble dry medicines and of dry medicines whose rates of solubility may not be controlled. The package also permits the bedside administration of other dry medicines at rates controlled by their rates of solubility.

Such barrier materials may include non-particulate-forming plastic filter materials, such as those manufactured by Millipore Filter Corporation and Gelman Corporation. These materials are available in a variety of porosities. For example, one such material is sold by Millipore Filter Corporation under the designation GSWP 025 00 GSO.45 micron and can be incorporated into the system to provide low rates of administration of soluble medicines. In some systems, the barrier 42 may be a very fine screen.

Means 34 forming the walls of the package 30 may be of either glass or another transparent thermoplastic material capable of aseptic treatment to insure sterile intravenous administration of the dry medicine.

A package 30 such as that shown in FIG. 2 operates as follows in IV systems of the type shown in FIG. 1. The package 30 is added to the system 10 of FIG. 1 by pressing its perforating conduit means 32 through the rubber IV stopper 18a. Because the level of the liquid 12c in the source of liquid 12 is higher than the container 30, fluid pressure provides a flow of liquid from the source 12 downwardly through the drip chamber 16, the flexible tubing 22a, the Y injection site 18, and upwardly through perforating conduit means 32 into the inner compartments of container 30. Because barrier 42 is pervious to air and liquid, liquid flows into compartment 36 and mingles with the dry medicine 38. The compartment 36 is completely filled because the fluid pressure will expel air or any other gaseous material within the container 30 outwardly through the air-pervious, liquid barrier 48 and air vent opening 46 formed in the container. The dry medicine 38 is thus exposed to the liquid of the system and is placed in solution. The liquid solution of dry medicine flows through the barrier 42 and outwardly through the perforating conduit means 32 of the package and into the Y injection site 18 and the flexible tube 22b to join the regulated flow of liquid through hypodermic needle 24 into the vein of the patient. The container 30 and compartment 36 are maintained full of liquid because they remain below the level 12c of liquid in the system.

In the system of FIGS. 1 and 2, therefore, the conduit of perforating conduit means 32 provides a two-way flow of liquid. At higher rates of administration, the higher specific gravity of the medicine solution can provide a significant outward flow under the influence of gravity, and as the medicine solution flows downwardly and outwardly of the cartridge 30, it is replaced by an upward flow of a less dense liquid from source 12, thus keeping the cartridge-like package 30 full of liquid as part of the system. The rate of flow of medicine solution from package 30 can be determined for very soluble medicines through selection of the porosity of barrier 42 and the diameter of the conduit in perforating conduit means 32. For example, where the barrier 42 has the porosity of laboratory filter paper, and the conduit of perforating conduit means 32 has a size at least that of a 16-gauge hypodermic needle, solutions of very soluble medicine can be administered from one gram doses within a time span of about two and one-half hours.

By reducing the porosity of the barrier 42, longer administration intervals may be obtained, and by increasing the porosity of the barrier, shorter administration intervals may be obtained. The rate of flow of medicine solution from the package may thus be determined and generally controlled by design of the package. The rate of flow of medicine solution from the package is not affected to a significant degree by any regulating clamp or pump that may be downstream of the package.

The package 30 provides a pocketless wall leading directly from the compartment for dry medicine to the conduit of the perforating conduit means. Cell-forming means 34 of package 30, for example, provides a frustoconical wall 34b at an acute angle (e.g., 30°) with respect to the axis of perforating conduit means 32. The medicine solution formed in compartment 36 can thus be substantially entirely drained from container 32 and administered to the patient. The package 30 in some circumstances may need to be supported or held in a generally vertical orientation for complete use of the container medicine.

Packages of the type shown in FIG. 2 may be manufactured by splitting the means 34 into two frustoconical wall portions, 34a forming the walls of a first cell or compartment, and 34b forming the walls of a second cell or compartment. Packages having a second cell are preferable to avoid concentrating the flow of medicine solution into a congested area of the barrier 42 and to avoid blockage of the congested area with undissolved medicine and a resultant restriction of flow of medicine. Thus, as shown in FIG. 2, an air and liquid-pervious barrier 42 may be interposed between portions 34a and 34b of the package. Splitting means 34 into two portions also permits the portion 34a forming the first cell 36 to be varied in size for different medicine dosages while maintaining a standard configuration for the other portion 34b that forms the second cell 40 and carries the connecting means 32. The connecting means 32 may be a tubular steel conduit molded into the end of portion 34b opposite the barrier and sharpened to provide an exposed, needle-like extremity. The opening 46 and housing for the air-pervious liquid barrier 48 may be molded into the portion 34a of the package. Such a cartridge-like package can have a maximum diameter on the order of about one inch for a medicine dose of about one gram.

Figure 3:
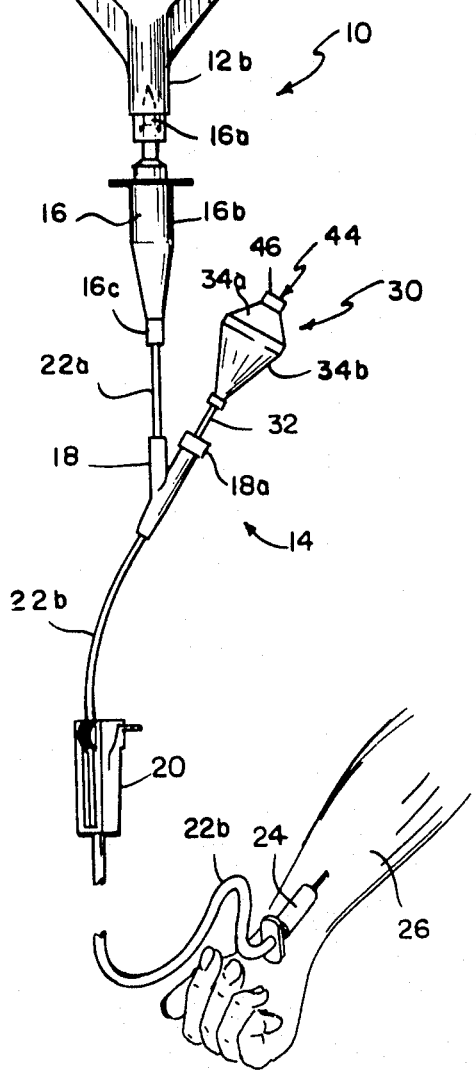
FIG. 3 is a cross-sectional view of another embodiment of the cartridge-like, dry-medicine package and container of this invention and the corresponding receptacle of the system.
Figure 3:
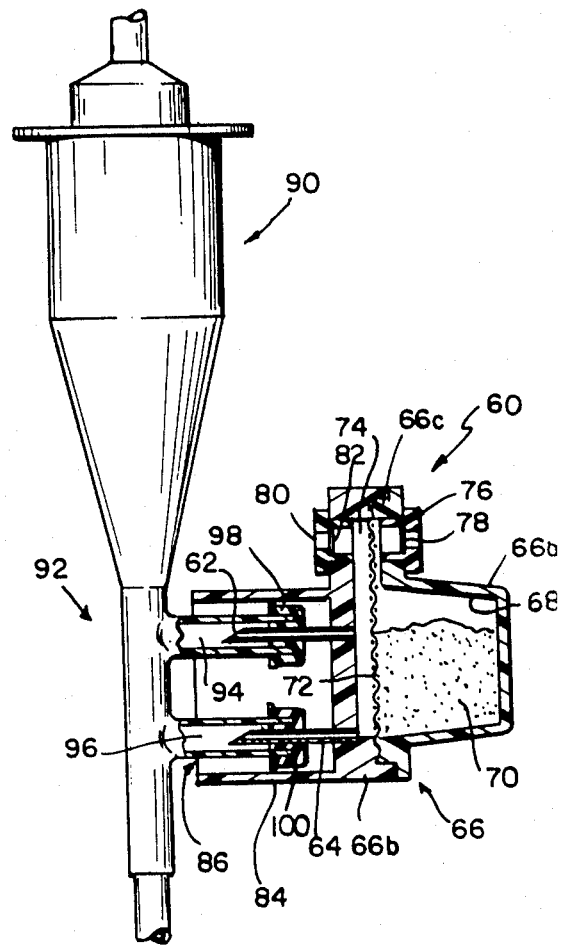

Another embodiment 60 of the cartridge-like package or container of this invention is shown in FIG. 3. The cartridge of FIG. 3 incorporates two needles as its perforating conduit means and two air vents. This embodiment is shown in FIG. 3 to use an especially designed drip chamber 90. The dual-needle system of FIG. 3 permits reduction of the size of the individual needles and, therefore, reduction of the size of the perforations created in the rubber IV stoppers of the system in use. Such a system can incorporate needles as perforating conduit means having a size comparable to 18- or 19-guage hypodermic needles.

Like package 30, package 60 includes a perforating conduit means, needles 62 and 64, wall-forming means 66 defining a first cell or compartment 68 for dry powdered medicine 70, and a liquid-pervious barrier 72 interposed between the dry medicine 70 and the perforating conduit means 62, 64.

The means 66 forming the container portion of the package 60 may be molded from glass or other clear thermoplastic material that is capable of aseptic treatment, and can include two portions 66a and 66b. The first portion 66a forms the first cell or compartment 68 for dry medicine 70 that may be varied in size. The second portion 66b carries the perforating conduit means 62, 64 and forms a second cell or compartment 74 within the package 60. The first package portion 66a and the second package portion 66b are adapted at their outer periphery 66c to provide a tongue and groove engagement to retain therebetween the barrier 72. The upper part of the first portion 66a of the package is formed to provide an air vent opening 76 for the first cell 68 and to carry an air-pervious, liquid barrier 78. The upper part of the second portion 66b of the package is formed to provide an air vent opening 80 for the second cell 74 and to carry an air-pervious, liquid barrier 82. Because both the first cell and second cell include air vents, the liquid-pervious barrier 72 need not be air-pervious. The air-pervious, liquid barriers 78 and 82 may be of the same type described above with respect to the cartridge of FIG. 2.

The second portion 66b of the package 60 can provide a standard element of the system with standard connecting means including a consistent spacing of the perforating conduit means 62, 64. The second portion may also include a projecting sleeve 84 surrounding and shielding perforating conduit means 62, 64. Sleeve 84 provides an opening 86 that may be sealed to avoid contamination of the perforating conduit means 62, 64 and protect against injury of personnel by the perforating conduit means in handling the cartridge.

As shown in FIG. 3, a drip chamber 90 may be especially adapted in its lower portion 92 to provide two projecting openings 94 and 96 sealed with standard rubber IV stoppers 98 and 100. The projecting openings 94 and 96 to the system are spaced a distance corresponding to the spacing between the needles 62 and 64 of cartridge 60. Sleeve 84 may be of such size that it guides the needles of perforating conduit means 62 and 64 into engagement with stoppers 98 and 100 when the cartridge 60 is added to the system. Cartridge 60 thus may support itself as shown in FIG. 3. Although FIG. 3 indicates that lower portion 92 of drip chamber 90 is adapted to accept the cartridge 60, the system may be provided with a receptacle-like portion 92 which is separate from the drip chamber.

As shown in FIG. 3, the portions 66a and 66b of container 60 form a pocketless wall leading from the first chamber 68 to the bore of the lower perforating conduit means 64 to avoid the entrapment of medicine solution within the package and to provide the medicine substantially entirely to the patient.

For a dose of about one gram, such a package may be formed to provide a first compartment 68 having a depth on the order of 1 of an inch from the barrier 72 to the distal wall of portion 66a. The outer walls of portion 66a are preferably frustoconical, having an average diameter of about one inch adjacent the barrier 72 and decreasing to about 1 of an inch at the distal wall. The second portion 66b of the package, which can comprise a standard cartridge head, carries two 18- or 19-guage needles 62, 64, each having an outside diameter of approximately 0.040 inch spaced typically somewhat over 1 of an inch apart. The needles 62, 64 project outwardly from portion 66b about 1 of an inch and are surrounded by a projecting sleeve 84 about 1 of an inch long. The outer sleeve 84 has, typically, the uniform thickness of about 0.060 inch and forms an opening approximately one inch in length and somewhat less than 1 of an inch in width that is centered upon the perforating conduit means 62, 64. The air vent openings 76 and 80 have an inside diameter on the order of one-fourth inch. The overall length of such a one gram cartridge is about two inches and its overall diameter is about one and 1 inch. The design and dimensions above may be varied for other configurations and dosages.

The embodiment of FIG. 3 will operate in a system the same as that shown in FIG. 1 in generally the same manner as the embodiment of FIG. 2. This can be visualized by substitution of the drip chamber 90 and cartridge 60 shown in FIG. 3 for the drip chamber 16 and cartridge 30 of FIG. 1. Since the container 60 in such a system will be entirely below the level 12c of the liquid in the source of liquid 12, upon addition of the cartridge 60 to the system and perforation of stoppers 98 and 100 by the needles 62, 64, the cartridge 60 will be filled entirely with liquid. Air from within compartments 68 and 74 will be expelled through openings 76 and 80, respectively. The dry medicine 70 in compartment 68 will be exposed to the liquid, and thereby placed in liquid solution. The medicine solution will flow through barrier 72 and outwardly through the bore of the lower perforating conduit means 64 and the opening 96 into the IV administration system. The container 60 will be maintained full of liquid by an inward flow through opening 94 of the system and the bore of upper perforating conduit means 62 into the interior of the cartridge. Such flow will continue until the medicine from within package 60 is substantially entirely delivered to the patient.

The receptacle 92 for the cartridge may have several configurations. It may provide an open passageway downwardly between projecting openings 94 and 96 so that liquid in the system can flow downwardly through the receptacle 92 in parallel with the flow through cartridge 60. The receptacle 92 may also be closed between projecting openings 94 and 96 so that the flow of liquid in the system is directed in its entirety through cartridge 60. Where there is no passageway in the receptacle 92 between projecting openings 94 and 96, a shunt comprising, for example, a second portion 66b of cartridge 60 that has been closed by a liquid-impervious solid wall in place of barrier 72, would normally be in place on the receptacle to permit flow in the absence of a cartridge. The receptacle may also include a valve (not shown) between the projecting openings 94 and 96 to permit selection of the above modes of operation of the system.

Figure 6:
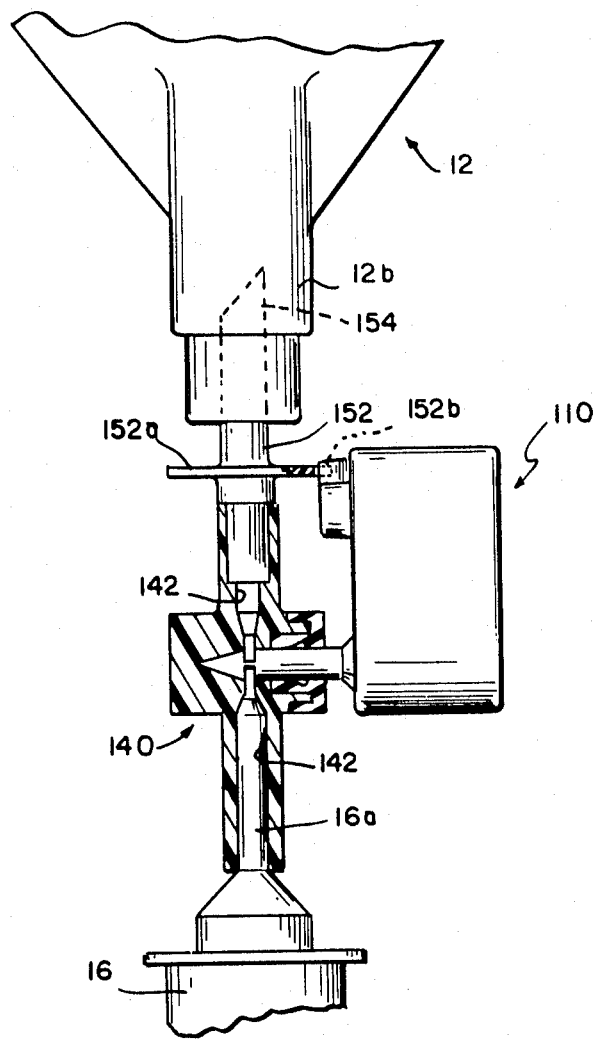
FIG. 6 is a partial view of an IV administration system with the cartridge and receptacle of FIGS. 4 and 5.
Figure 5:
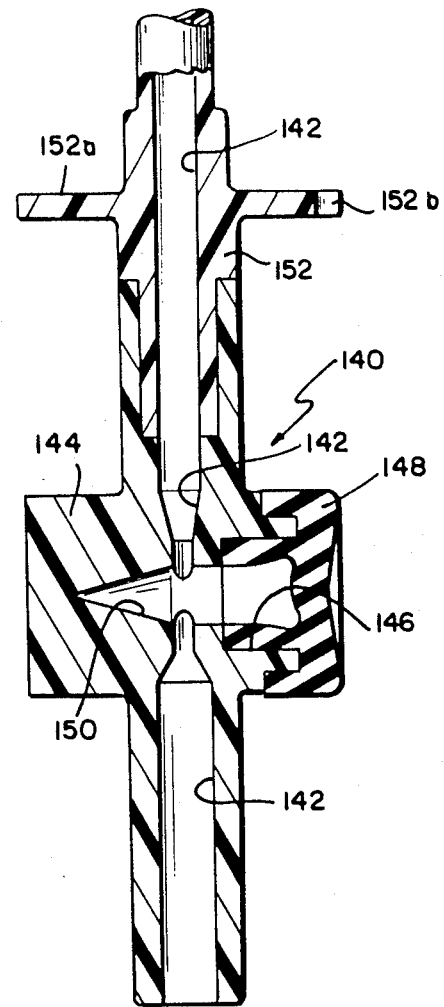
FIG. 5 is a cross-sectional view of a receptacle for use with the package and cartridge of FIG. 4.
Figure 4:
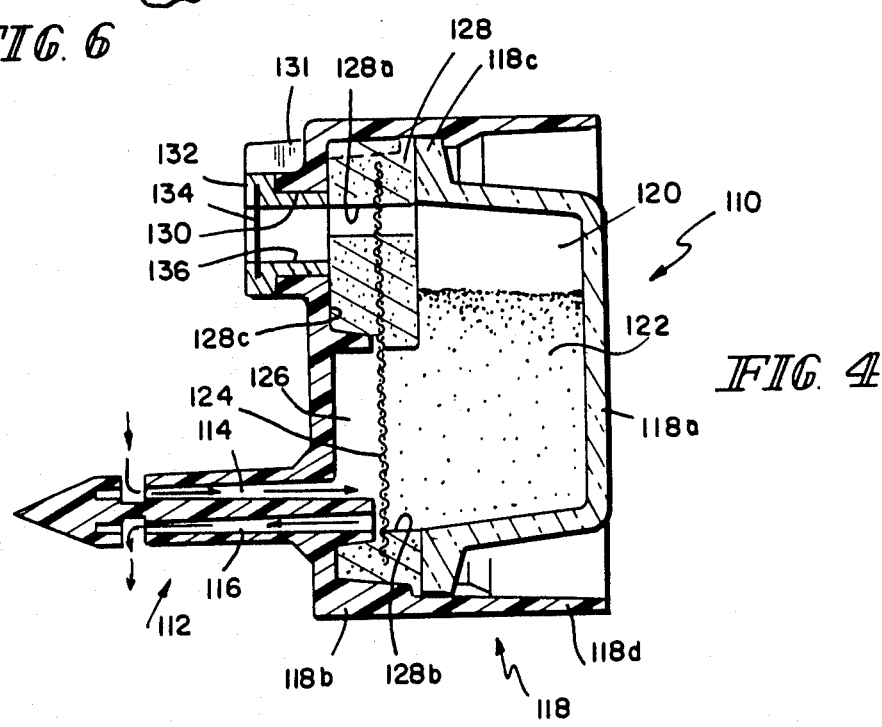
FIG. 4 is a cross-sectional view of still another embodiment of the cartridge-like, dry medicine package and container of this invention.

Still another embodiment 110 of the cartridge-like package or container of this invention is shown in FIG. 4. The cartridge of FIG. 4 incorporates a single spike or needle 112 having two passages 114 and 116 as its perforating conduit means and a single air vent. This embodiment uses an especially designed adapter and receptacle 140, as shown in FIG. 5 and FIG. 6. When cartridge 110 with its multiple-passage perforating conduit means 112 is inserted into receptacle 140 as shown in FIG. 6, the flow of liquid in the system is directed in its entirety through cartridge 110. The engagement of perforating conduit means 112 with receptacle 140 closes the passage 142 (FIG. 5) of the receptacle, and liquid enters the cartridge 110 through passage 114 and carries the dissolved medicine back to the IV administration system through passage 116.

Like packages 30 and 60, package 110 includes a perforating conduit means 112, wall-forming means 118 defining a first cell or compartment 120 for dry powdered medicine 122, and a liquid-pervious barrier 124 interposed between the dry medicine 122 and the perforating conduit means 112.

The means 118 forming the container portion of the package 110 may be molded from glass or other clear thermoplastic material that is capable of aseptic treatment, and can include two portions 118a and 118b. The first portion 118a forms the first cell or compartment 120 for dry medicine 122 that may be varied in size. The first portion 118a is preferably glass. The second portion 118b forms the perforated conduit means 112 and can form a second cell or compartment 126 within the package 110. The second portion 118b may be ABS, rigid polyethylene or polypropylene or other suitable polymeric material.

The first package portion 118a and the second package portion 118b are adapted at their outer periphery 118c to provide a tongue and groove engagement. The barrier 124 is carried in a gasket 128 of elastomeric material, such as natural rubber. The gasket 128 is retained between the first portion 118a and second portion 118b upon assembly of the package 110. Two openings 128a and 128b are formed in the gasket 128 and are closed by barrier 124 to the dry medicine 122 but not to air or liquid. Gasket 128 includes a sealing surface 128c between openings 128a and 128b that engages and seals against the portion 118b, thereby defining cell 126 between portion 118b and the barrier 124.

The upper part of the second portion 118b of the package is formed to provide an air vent opening 130 for the interior of the package 110. An insert 132 that may be formed of a rigid moldable plastic carries an air-pervious, liquid barrier 134 in the air vent opening 130. Openings 130 and 128a permit the air or gas within compartments 126 and 120 to be expelled from within the package 110 through the opening 136 of insert 132 and permit medicine compartment 120 to be completely filed with liquid solution. Because the air-pervious barrier 134 is liquid-impervious, the liquid will not escape the cartridge 110. The air-pervious, liquid barrier 134 may be of the same type described above with respect to the cartridge of FIG. 2.

As shown in FIG. 5, a receptacle 140 may have an especially adapted semi-rigid bottom portion 144 to provide a projecting opening 146 sealed with a standard rubber stopper 148. The portion 144 forms a socket 150 shaped to mate the perforating conduit means 112 of the cartridge.

The receptacle 140 provides an adapter to permit the use of the dry medicine package 110 with standard IV components. FIG. 6 shows the use of receptacle-adapter 140 and the manner in which its ends are adapted for insertion into such a standard IV system. In adapting a standard IV system to use packages 110, the receptacle 140 is first placed upon the spike-like conduit means 16a of the drip chamber 16 of a standard IV administration set, such as that shown in FIG. 1, by inserting the spike-like conduit means 16a into the bottom portion of passageway 142. The top portion 152 of receptacle 140 is rigid and forms a sharpened spike 154 about passageway 142. The spike 152 is used to perforate, enter, and provide a sealed engagement at its periphery with the conduit-like closure 12b of solution container 12. The upper portion 152 of the receptacle is provided with an extended surface 152a to assist the user in inserting the receptacle into the solution container 12. With the receptacle 140 in place, liquid from the solution container 12 may flow freely through passageway 142 of the receptacle.

Cartridge 110 and its dry medicine is placed in the IV system by perforating stopper 148 with the perforating conduit means 112 and seating it in socket 150 of the adapter 140. The cartridge 110 has a key 131 formed by portion 118b adjacent the air vent opening 130. The extended surface 152a of the receptacle 152 is formed with a slot 152b into which key 131 of the cartridge is inserted. Cartridge 110 may thus be supported as shown in FIG. 6. The perforating conduit means 112 when seated in socket 150 closes and substantially seals passage 142. Liquid above the socket 150 is then urged by gravity to flow through cartridge 110 by entering the upper passage 114 of the perforating conduit means 112 and leaving the lower passage 116. The container 110 can thus be filled with liquid and provide dry medicine in solution to the patient.

For a dose of about one gram, such a package may be formed to provide a first compartment 120 having a depth on the order of ⅜ of an inch from the barrier 124 to the distal wall of portion 118a. The outer walls of portion 118a are preferably frustoconical, having an average diameter of about one inch adjacent the barrier 124 and decreasing to about ¼ of an inch at the distal wall. The second portion 118b forms needle 112 having a length of about an inch and an outside diameter of approximately 0.190 inch. The forward surface of needle 112 forms a cone with a solid angle of 40° at its apex to assist in perforation of stopper 148. The conduit 114 and 116 extend forwardly within the needle 112 and terminate adjacent the base of the conical forward end. Openings for the conduits 114 and 116 are formed by two slots across the needle 112 having a depth sufficient to intercept the conduits 114 and 116. The second portion 118b of the cartridge may be formed with a cylindrical skirt 118d that extends around and protects the first portion 118a from contact. The air vent opening 130 has an inside diameter on the order of one-fourth inch. The overall length of such a one gram cartridge is about two inches and its overall diameter is about one and ½ inches. The design and dimensions above may be varied for other configurations and dosages.

The embodiment of FIG. 4 will operate in a system in generally the same manner as the embodiments of FIG. 2 and FIG. 3. Since the container 110 in such a system will be entirely below the level of the liquid in the source of liquid 12, upon addition of the cartridge 110 to the system and the perforation of stopper 148 by the needle 112, the cartridge 110 will be filled entirely with liquid. Air from within compartments 120 and 126 will be expelled through openings 128a and 136, respectively. The dry medicine 122 in compartment 120 will be exposed to the liquid, and thereby placed in liquid solution. The medicine solution will flow through barrier 124 and outwardly through the lower conduit 116 into the IV administration system. The container 110 will be maintained full of liquid by an inward flow through the upper conduit 114 into the interior of the cartridge. Such flow will continue until the medicine from within package 110 is substantially entirely delivered to the patient.

The system of this invention thus includes a package or container adapted for cartridge-like addition to an IV administration system. The connecting means by which the cartridge-like container may be added to the system is preferably a perforating conduit means. The perforating conduit means may be a hypodermic needle which is usable with standard Y injection sites of IV sets or a molded plastic spike adapted to mate a socket-forming adapter for addition to standard IV sets.

The invention may be used, for example, to permit the treatment of diseases that require periodic high blood concentrations of antibiotic medicine, and permit such concentrations from dry antibiotic medicines at planned, periodic intervals. The invention may provide an opportunity to kill bacteria which require high antibiotic concentrations. Such a system may be particularly adapted for use with cephalothin sodium antibiotics such as those sold by Eli Lilly and Company under the trademark KEFLIN and may provide periodic high blood concentration of the antibiotic by administering the medicine in solutions over short intervals. The system is not limited to antibiotics, but also provides means to deliver other dry medicines, for example, cardiovascular drugs and others, in a variety of dosages. The system is capable of design to provide many rates of administration. Since the medicine is administered directly from its package, it may be stored and used by hospital personnel without resort to the hospital pharmacist.

The preferred embodiments of my invention described above are capable of many modifications. Changes in the construction and arrangement may be made without departing from the spirit and scope of my invention as disclosed in the following claims.

What is claimed is:

1. A system for the sterile intravenous administration of dry medicine comprising:
   a source of liquid,
   means to inject liquid into a human vein,
   means forming an injection passageway between the source of liquid and the injection means,
   a receptacle forming a socket and a receptacle passageway between the source of liquid and the means forming an injection passageway,
   a valve to control the flow of liquid through the injection passageway, and
   a cartridge-like package adapted for use with the system and including conduit means adapted to perforate and communicate with the injection passageway, means forming a cell for dry, particulate medicine with a liquid-pervious barrier to the dry medicine at one end and an air vent with an air-pervious, liquid barrier, the perforating conduit means being in communication with said one end of the cell whereby, upon perforation of the passageway means by the perforating conduit means below the source of liquid, the cell fills with liquid, the medicine is placed in solution in the liquid, and the medicine solution flows into the vein,
   the perforating conduit means of the cartridge-like package being adapted to engage the socket of said receptacle, to close the receptacle passageway and to provide two channels for liquid, one channel leading from said source of liquid to the cartridge cell and the other channel leading from the cartridge cell to the means forming an injection passageway to said injection means.

2. The system of claim 1 wherein said receptacle is adapted at one end to pierce the source of liquid and adapted at the opposite end to receive removably the means forming an injection passageway to said injection means.

3. A method of administration of dry medicine intravenously in liquid solution comprising:
   enclosing a dry, particulate medicine in a sterile package that is open to atmospheric pressure behind a liquid-pervious barrier to the dry medicine,
   placing the sterile package in communication with a source of liquid and a passageway for said liquid to the vein of a patient, said package being entirely below the level of liquid in the source,
   admitting the liquid into the package and maintaining the package full of liquid under the influence of the fluid pressure of the system and dissolving the dry medicine within the package to form a medicine solution, the liquid being admitted into the package through one conduit and the medicine solution passing outwardly to the passageway through a second conduit, both conduits being formed in a single needle on the package, said needle intercepting flow of liquid from the liquid source to the vein so that all liquid from the source passes through said package, and
   allowing the solution of medicine and liquid to pass continuously through the barrier and from the package into the passageway while providing a continuous flow of replacement liquid into the package until the medicine solution is exhausted from the package.

4. The method of claim 3 including the step of providing a continuous flow of liquid that is parallel and additive to the flow of medicine solution from the package.

5. A package adapted for the sterile intravenous administration of dry medicine in solution, comprising perforating conduit means forming at least two passageways, means forming a first cell for dry, particulate medicine and a second cell in communication with the passageways of the perforating conduit means, and a liquid-pervious barrier to the dry, particulate medicine separating the first and second cells, the means forming the cells also forming an air vent and having two portions, the perforating conduit means being formed in one portion in communication with the second cell of the package, and the dry medicine being carried by the other portion, the barrier being carried in a gasket held between said first portion and second portion to form thereby the two cells, the gasket forming two openings and a sealing surface between the two openings that engages the one portion, the gasket defining in part the second cell of the package, the air vent being formed in the one portion opposite the perforating conduit means and in communication with one of the openings of gasket so that upon the introduction of liquid to the package air is expelled from the first and second cells through the air vent.

6. A system for the intravenous administration of dry medicine, comprising
   a dry medicine package including perforating conduit means forming at least two passageways, means forming a cell for dry, particulate medicine in communication with the passageways of the perforating conduit means, and a liquid-pervious barrier to the dry, particulate medicine separating the perforating conduit means and the cell, said means forming the cell also forming an air vent, and
   a receptacle for said dry medicine package adapted at its ends for insertion into a intravenous administration system, said receptacle forming a socket and a passageway through the socket generally along its central axis, said socket being sealed by an elastomeric stopper,
   said perforating conduit means being adapted to perforate said stopper and to mate said socket, substantially closing and sealing the receptacle passageway and positioning the passageways of the perforating conduit means in communication with receptacle passageway above and below, respectively, the socket.

7. The system of claim 6 wherein cell-forming means has two portions and forms two cells, the perforating conduit means is formed in one portion in communication with the second cell of the package, and the dry medicine is carried by the other portion with the barrier carried in a gasket between said first portion and second portion to form thereby the two cells.

8. The system of claim 7 wherein the gasket forms two openings and a sealing surface between the two openings that engages the one portion and defines in part the second cell of the package, and the air vent is formed in the one portion opposite the perforating conduit means and in communication with one of the openings of gasket so that upon the introduction of liquid to the package air is expelled from the first and second cells through the air vent.

9. The system of claim 6 wherein the means forming a cell of dry particulate medicine forms a key on its outer surface, and the receptacle forms a slot on its outer surface, and said cartridge key may be engaged in the receptacle slot to retain the position of the cartridge in the receptacle upon insertion.

* * * * *

UNITED STATES PATENT AND TRADEMARK OFFICE
CERTIFICATE OF CORRECTION

PATENT NO. : 4,465,471
DATED : August 14, 1984
INVENTOR(S) : Dale C. Harris and William W. Hargrove It is certified that error appears in the above-identified patent and that said Letters Patent is hereby corrected as shown below:

In line 63 of the "Related U.S. Application Data" on first page, "Apr. 26" should be --Aug. 26--.

Column 1, line 6, "Apr. 26" should be --Aug. 26--.

Column 4, line 55, "examle" should be --example--.

Signed and Sealed this

Fifth Day of March 1985

[SEAL]

Attest:

DONALD J. QUIGG

Attesting Officer     Acting Commissioner of Patents and Trademarks